US00PP14499P29

(12) United States Plant Patent
Trees

(10) Patent No.: US PP14,499 P2
(45) Date of Patent: Jan. 27, 2004

(54) DIASCIA PLANT NAMED 'BALWHISALIM'

(50) Latin Name: *Diascia barberae*
Varietal Denomination: Balwhisalim

(75) Inventor: Scott C. Trees, Arroyo Grande, CA (US)

(73) Assignee: Ball Floraplant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/329,628

(22) Filed: Dec. 26, 2002

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—Wood, Phillips, Katz, Clark & Mortimer

(57) ABSTRACT

A new and distinct Diascia plant named 'Balwhisalim', characterized by its light pink colored flowers, spreading, trailing growth habit, and medium green foliage.

2 Drawing Sheets

Latin name of genus and species of plant claimed: *Diascia barberae.*
Variety denomination: 'Balwhisalim'.

BACKGROUND OF INVENTION

The present invention comprises a new and distinct Diascia plant, botanically known as *Diascia barberae,* and hereinafter referred to by the cultivar name 'Balwhisalim'.

The new cultivar was developed by the inventor in a controlled breeding program during November 1999, at Arroyo Grande, Calif. The objective of the breeding program was the development of Diascia cultivars with a well-branched, spreading growth habit, continuous flowering and medium green foliage.

The new cultivar was the result of open pollination with the female parent being the commercially available Diascia variety 'Red Start'. 'Balwhisalim' was discovered and selected in February 2000 as a single flowering plant from within the progeny of the above stated cross and was designated NCT-48B.

Asexual reproduction of the new cultivar at West Chicago, Ill. was carried out by the use of terminal stem cuttings and has demonstrated that the characteristics of the new cultivar as herein described are firmly fixed and retained through successive generations of such asexual propagation.

SUMMARY OF INVENTION

It was found that the cultivar of the present invention:

(a) exhibits light pink colored flowers, (b) forms foliage of a medium green color, and (c) exhibits a spreading, trailing growth habit.

The new cultivar can be compared to its female parent, the commercially available Diascia plant 'Red Start' (non-patented). In side-by-side comparison, plants of the new cultivar are more vigorous with a taller and more spreading growth habit than plants of 'Red Start'.

BRIEF DESCRIPTION OF PHOTOGRAPH

The accompanying photographs show as nearly true as it is reasonably possible to make the same in color illustrations of this type, typical flower and foliage characteristics of the new cultivar. The plants were grown for 9 weeks in a greenhouse at West Chicago, Ill.

DETAILED BOTANICAL DESCRIPTION

Figure 1:
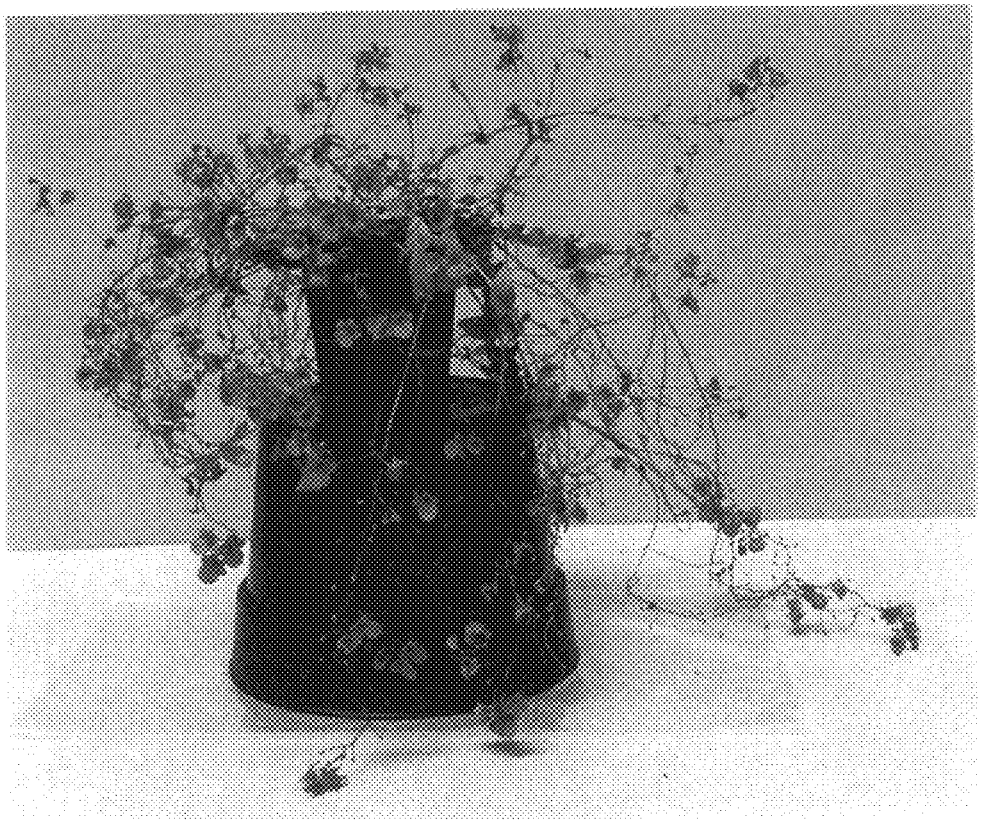
FIG. 1 illustrates the overall growth habit of the new cultivar.
Figure 2:
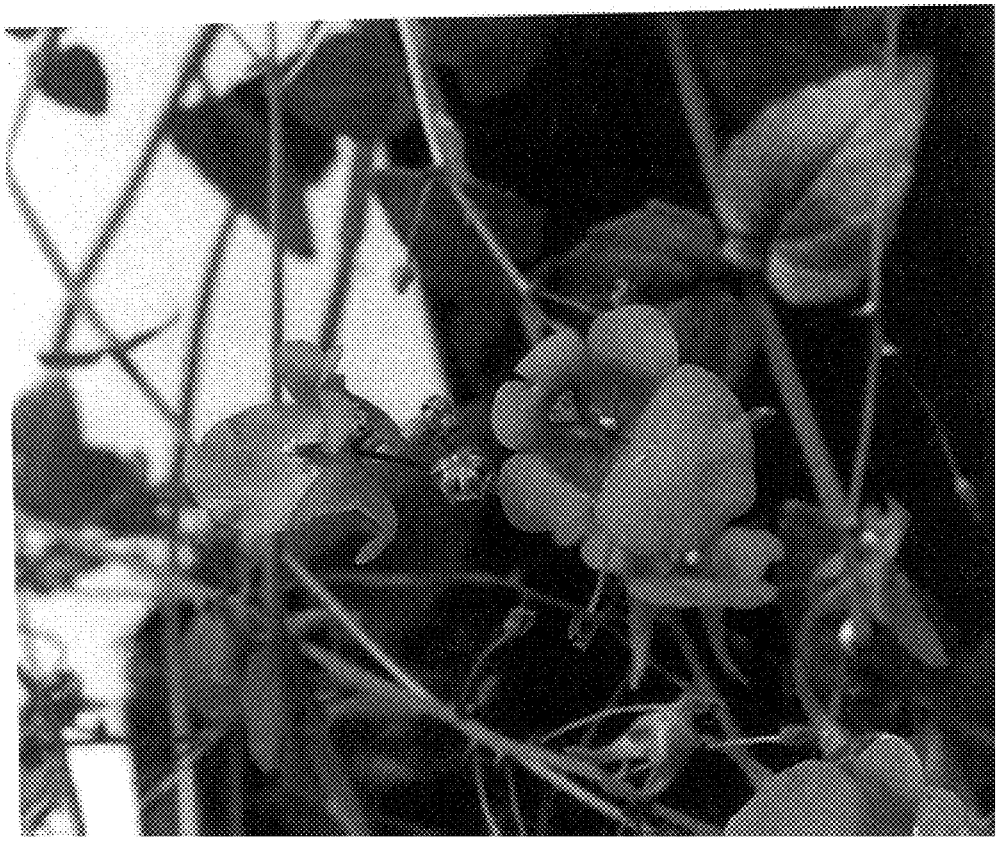
FIG. 2 illustrates a close up view of individual flowers of the new cultivar.

The new cultivar has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Apr. 24, 2002. The readings were taken between 1:00 and 3:00 p.m. under natural daylight conditions. The plants were produced from cuttings taken from stock plants and were grown in a double polycarbonate covered greenhouse under conditions comparable to those used in commercial practice. The plants were grown for 9 weeks while utilizing a soilless growth medium and maintaining temperatures of approximately 62° to 75° F. (17° to 24° C.) during the day and approximately 52° to 60° F. (11° to 15° C.) during the night and light levels of 5,000 to 8,000 footcandles.

Classification:
*Botanical.*—*Diascia barberae* cultivar 'Balwhisalim'.
Parentage:
*Open pollination.*—Female Parent — Commercially available Diascia variety 'Red Start'.
Propagation:
*Type cutting.*—Terminal tip.
*Time to initiate roots.*—Approximately 14 to 21 days.
*Root description.*—Fibrous, branching.

Plant description:

*Crop time.*—Approximately 5 to 7 weeks from planting of rooted cuttings in a 10 cm pot.

*Habit of growth.*—Vigorous. Pinching improves branching. A mature plant, 9 weeks after the planting of a rooted cutting, measures approximately 25.3 cm in height and approximately 68 cm in width with approximately 4.4 main branches and 72 lateral flowering branches.

*Form.*—Spreading, trailing.

*Lateral branch.*—Shape: Square. Length: Approximately 17.3 cm. Diameter: Approximately 1.4 mm. Internode length at middle of branch: Approximately 2.8 cm. Texture: Sparsely glandular-pubescent. Color: 144A with glands of 93A.

*Foliage.*—Type: Simple. Arrangement: Opposite. Shape: Ovate. Margin: Serrate. Apex: Acute. Base: Cordate. Texture: Glabrous, supple. Quantity per lateral branch: Approximately 10.8. Leaf length: Approximately 2.4 cm. Leaf width: Approximately 1.7 cm. Leaf orientation to stem: Acute. Leaf fragrance: None. Upper surface of mature foliage is closest to 137A and lower surface is lighter than 147B. Upper and lower surfaces have pinnate venation of 143C. Petiole length: Approximately 4 mm. Petiole diameter: Approximately 2 mm. Petiole color: 143C. Upper and lower surfaces of petiole are glabrous.

Flowering description:

*Flowering habit.*—Freely flowering.

*Natural flowering season.*—Year round in greenhouse environment and spring through autumn in outdoor garden.

*Flower arrangement.*—Terminal racemes.

Flower description:

*Type.*—Solitary, five lobed and zygomorphic.

*Fragrance.*—None.

*Aspect.*—Concave.

*Corolla.*—Width: Approximately 1.8 cm. Length: Approximately 1.9 cm. Depth: Approximately 4 mm.

*Petals.*—Number: Five, fused at base. Aspect: Cupped. Two upper petals: Length is approximately 4 mm, width is approximately 4 mm. Lateral petals: Length is approximately 5 mm, width is approximately 6 mm. Slightly curved nectar spurs originate from base of lateral petals. Nectar spur length: Approximately 7.6 mm. Nectar spur color: 50D with venation of 79C. Lower petal: Length is approximately 1 cm, width is approximately 1.2 cm. All petals: Margin: Entire. Apex: Obtuse. Texture: Glabrous. Color: Upper surface of upper petal is closest to 51B at margin with 79D and venation of 79A at base and indentation at base of 1A. Lower surface of upper petal is 51C. Upper surface of lateral petals is closest to 51B at margin with 79D and venation of 79A at base. Lower surface of lateral petals is 51C. Upper surface of lower petal is 51B with slight glandular pubescence at base. Glands are 93A. Lower surface of lower petal is 51C at margin and 50D at base.

*Sepals.*—Quantity: 5. Shape: Lanceolate. Length: Approximately 3 mm. Width: Approximately 1 mm. Apex: Acute. Margin: Entire. Calyx shape: Star. Calyx diameter: Approximately 6 mm. Calyx texture: Densely glandular-pubescent with glands of 93A on outer surface. Inner surface is glabrous. Color of both inner and outer surface is 143A.

*Pedicel.*—Length: Approximately 8 mm. Width: Less than 1 mm. Strength: Moderate. Texture: Moderately glandular-pubescent. Color: 143A with glands of 93A.

*Peduncle.*—Length: Approximately 5.4 cm. Diameter: Approximately 1.1 mm. Aspect: At acute angle to branch. Texture: Sparsely glandular-pubescent. Color: 143A with glands of 93A.

*Bud.*—Shape: Oval, flat. Length: Approximately 5.3 mm in length. Diameter: Approximately 5 mm. Color: 2D.

*Reproductive organs.*—Androecium: There are 4 stamens. Stamen length: Approximately 3 mm. Filament color: closest to 96C. Anther shape: Oval. Anther length: Lessa than 1 mm. Anther color: 2B. Pollen amount: Abundant. Pollen color: 6B. Gynoecium: There is one pistil, 3 mm in length. Stigma shape: Round. Stigma length: Less than 1 mm. Stigma color: 144D, transparent. The style length is approximately 1.5 mm and the color is 144C. Ovary length is approximately 1.5 mm and color is 144B.

Seed production: Seed production has not been observed.

Disease resistance: Resistance to pathogens has not been observed.

Hardiness zone: 'Balwhisalim' is hardy in zones nine (9) and above.

I claim:

1. A new and distinct *Diascia barberae* plantnamed 'Balwhisalim' substantially as herein shown and described, which:

(a) exhibits light pink colored flowers, (b) forms medium green foliage, and (c) exhibits a spreading and trailing growth habit.

* * * * *